United States Patent [19]
Gargan et al.

[11] Patent Number: 6,080,384
[45] Date of Patent: Jun. 27, 2000

[54] METHODS FOR RADIONUCLIDE-LABELING OF BIOMOLECULES AND KITS UTILIZING THE SAME

[75] Inventors: Paul E. Gargan, Granger; John D. Scheu, South Bend, both of Ind.

[73] Assignee: American Biogenetic Sciences, Inc., Copiague, N.Y.

[21] Appl. No.: 08/827,013

[22] Filed: Mar. 25, 1997

[51] Int. Cl.$^7$ ............................. A61K 51/00; A61M 36/14
[52] U.S. Cl. .......................... 424/1.69; 534/10; 424/1.11; 424/1.65
[58] Field of Search .................................. 424/1.11, 1.49, 424/1.65, 1.69, 9.1, 9.3, 9.4, 9.5, 9.6; 530/300, 333–334, 338, 311, 317; 534/7, 10–16; 206/223, 569–570

[56] References Cited

U.S. PATENT DOCUMENTS

| | | |
|---|---|---|
| Re. 35,457 | 2/1997 | Rhodes ................................... 424/1.49 |
| Re. 35,500 | 5/1997 | Rhodes ................................... 424/1.49 |
| 4,305,922 | 12/1981 | Rhodes . |
| 4,311,688 | 1/1982 | Burchiel et al. . |
| 4,323,546 | 4/1982 | Crockford et al. . |
| 4,331,647 | 5/1982 | Goldenberg . |
| 4,348,376 | 9/1982 | Goldenberg . |
| 4,421,735 | 12/1983 | Haber et al. . |
| 4,424,200 | 1/1984 | Crockford et al. . |
| 4,472,371 | 9/1984 | Burchiel et al. . |
| 4,479,930 | 10/1984 | Hnatowich . |
| 4,647,445 | 3/1987 | Lees . |
| 4,652,440 | 3/1987 | Paik et al. . |
| 4,666,698 | 5/1987 | Schwarz . |
| 4,668,503 | 5/1987 | Hnatowich . |
| 4,670,545 | 6/1987 | Fritzberg et al. . |
| 4,877,868 | 10/1989 | Reno et al. . |
| 5,053,493 | 10/1991 | Pak et al. . |
| 5,061,641 | 10/1991 | Shochat et al. . |
| 5,078,985 | 1/1992 | Rhodes . |
| 5,080,883 | 1/1992 | Lyle et al. . |
| 5,102,990 | 4/1992 | Rhodes . |
| 5,116,596 | 5/1992 | Bremer et al. . |
| 5,164,175 | 9/1992 | Bremer et al. . |
| 5,177,192 | 1/1993 | Pak et al. . |
| 5,225,180 | 6/1993 | Dean et al. . |
| 5,277,893 | 1/1994 | Rhodes . |
| 5,317,091 | 5/1994 | Subramanian . |
| 5,328,679 | 7/1994 | Hansen et al. . |
| 5,334,708 | 8/1994 | Chang et al. . |
| 5,346,687 | 9/1994 | Rhodes . |

FOREIGN PATENT DOCUMENTS

| | | |
|---|---|---|
| 0 237 150 | 9/1987 | European Pat. Off. . |
| 0 271 806 | 6/1988 | European Pat. Off. . |
| 0 336 678 | 10/1989 | European Pat. Off. . |
| 0 403 225 | 12/1990 | European Pat. Off. . |
| 0 419 203 | 3/1991 | European Pat. Off. . |
| WO 85/03231 | 8/1985 | WIPO . |
| WO 87/04164 | 7/1987 | WIPO . |
| WO 88/07382 | 10/1988 | WIPO . |

OTHER PUBLICATIONS

Gargan and Bell, 1994, "Diagnostic Capacity of Tc–99m Mh1–Fab'0 for the Detection of Thrombi in Humans. A New Thrombus Specific Monoclonal Antibody Fragment," J. Nucl. Med. Abstract Book, Proceedings of the 41$^{st}$ Annual Meeting, Orlando, Florida, Jun. 5–8 35(5): Abstract No. 314.
Gargan et al., "Rapid Imaging of Pulmonary Emboli with Technetium 99M–Labeled Fragment of the Antifibrin Antibody, MH1," Thrombosis and Haemostasis, Abstract, XIVth Congress of the International Society on Thrombosis and Haemostasis, New York, New York, Jul. 4–9, p. 1356.
Pak et al., 1992, "An Instant Kit Method for Labeling Antimyosin Fab' with Technetium–99m: Evaluation in an Experimental Myocardial Infarct Model", J. Nucl. Med. 33:144–149.
Rhodes, 1991, "Direct Labeling of Proteins with $^{99m}$Tc", Nucl. Med. Biol. 18:667–676.
Rhodes et al., 1986, "Technetium–99m Labeling of Murine Monoclonal Antibody Fragments", J. Nucl. Med. 27:685–693.
Schwarz and Steinstrasser, 1987, "A Novel Approach to Tc–99m–Labeled Monoclonal Antibodies", Society of Nuclear Medicine 28:721 (No. 695).
Thakur and DeFulvio, 1991, "Technetium–99m–Labeled Monoclonal Antibodies for Immunoscintigraphy", J. Immunol. Meth. 137:217–224.
Thakur et al., 1990, "Use of Ascorbic Acid(AA) for Direct TC–99 Labeling of Monoclonal Antibodies(MAbs)", Eur. J. Nucl Med. 16:392 (No. 8).
Verbruggen, 1990, "Radiopharmaceuticals: State of the Art", Eur. J. Nucl. Med. 17:346–364.
Wong et al., 1978, "A Rapid Chemical Method of Labeling Human Plasma Proteins with $^{99m}$Tc–Pertechnetate at pH 7.4", Int. J. Appl. Radiation and Isotopes 29:251–253.
Bickerstaff and Zhou, 1993, "Protease Activity and Autodigestion (Autolysis) Assays Using Coomassie Blue Dye Binding", Anal. Biochem. 210:155–158.
Gargan et al., 1993, "Rapid Imaging of Pulmonary Emboli with a Technetium–99m–Labeled Fragment of the Antifibrin Antibody, MH1", THHADO 69:1356.
Griffiths et al., 1994, "Preparation of a Pure $^{99m}$Tc–F(ab')$_2$ Radioimmunoconjugate by Direct Labeling Methods", Nucl. Med. Biol 21:649–655.
Griffiths et al., 1992, "Radiolabeling of Monoclonal Antibodies and Fragments with Technetium and Rhenium", Bioconjugate Chem. 3:91–99.
Mather and Ellison, 1990, "Reduction–Mediated Technetium–99m Labeling of Monoclonal Antibodies", J. Nucl. Med. 31:692–697.
Pak et al., 1989, "A Rapid and Efficient Method for Labeling IgG Antibodies with Tc–99m and Comparison to Tc–99m FAB' Antibody Fragments", J. Nucl. Med. 30:793 (No. 268).

*Primary Examiner*—José G. Dees
*Assistant Examiner*—Dameron Jones
*Attorney, Agent, or Firm*—Pennie & Edmonds LLP

[57] ABSTRACT

Novel methods for radiolabeling sulfhydryl group-bearing biomolecules, novel compositions useful for radiolabeling sulfhydryl group-bearing biomolecules, kits comprising such novel compositions and methods for imaging mammalian, preferably human, tissue employing radiolabelled biomolecules are described. The methods, compositions and kits of the present invention are useful for labeling sulfhydryl group-bearing biomolecules such as whole molecule proteins, protein fragments or peptides, in particular, monoclonal or polyclonal antibodies, and especially, antifibrin MH1 monoclonal antibody.

45 Claims, 1 Drawing Sheet

FIG. 1

METHODS FOR RADIONUCLIDE-LABELING OF BIOMOLECULES AND KITS UTILIZING THE SAME

1. FIELD OF THE INVENTION

The present invention relates to novel compositions useful for the radionuclide labeling of a sulfhydryl group-bearing biomolecule, methods for labeling a sulfhydryl group-bearing biomolecule, kits comprising such novel compositions and methods for imaging tissue of a mammal, preferably human, patient or subject using radionuclide-labeled biomolecules.

2. BACKGROUND OF THE INVENTION

Radiolabeling of biomolecules, in particular peptides, and most particularly monoclonal or polyclonal antibodies, has been used as a means to track and detect the pathway or location of a particular peptide when administered to a patient or subject. Such radiolabelled peptides are capable of emitting low levels of gamma radiation, which can be detected and pin-pointed to a target organ or other substrate.

Radionuclides such as rhenium-186m and particularly, technetium-99m, are useful for biomolecule labeling since they are known to form relatively stable bonds with a sulfhydryl group thereof. However, for sulfhydryl group-bonding to occur, rhenium-186m and technetium-99m must be in the +3, +4 or +5 oxidation state. Because technetium-99m is most readily available as its pertechnetate-99m salt, i.e., a form of technetium having a +7 oxidation state, most technetium-99m species must be reduced prior to reaction with a sulfhydryl group.

The labeling of biomolecule sulfhydryl groups via reduction of pertechnetate-99m salt has been performed using stannous ($Sn^{2+}$) ion as a reducing agent for technetium-99m. In particular, aqueous solutions of stannous ion formed from acidic solutions (D. W. Wong et al., *Int. J. appl. Radiat. Isotopes*, 29, 251 (1978); A. Schwarz et al., Abstract No. 695 from the "Proceedings of the 34th Annual Meeting," *J. Nucl. Med.*, Vol. 28, No. 4, April 1987; B. A. Rhodes, *Nucl. Med. Biol.*, 18(7), 667 (1991); G. L. Griffiths et al., *Bioconjugate Chem.*, 3(2), 91 (1992); EP Patent Application 403 225 to Immunomedics, Inc.; U.S. Pat. No. 4,305,992 to Rhodes and U.S. Pat. No. 5,334,708 to Chang et al.); stannous ion in the presence of tartrate anion (B. A. Rhodes et al., *J. Nucl. Med.*, 27(5), 685 (1986); G. L. Griffiths et al., *Nucl. Med. Biol.*, 21(4), 649 (1994); U.S. Pat. No. 5,061,641 to Shocat et al.; U.S. Pat. No. 4,877,868 to Reno et al.; U.S. Pat. Nos. 5,346,687, 5,277,893, 5,102,990 and 5,078,985 to Rhodes; U.S. Pat. Nos. 4,424,200 and 4,323,546 to Crockford et al.; U.S. Pat. Nos. 4,472,371 and 4,311,688 to Burchiel et al.; U.S. Pat. No. 5,328,679 to Hansen et al.; and EP Patent Applications 419 203 and 336 678 to Immunomedics, Inc.); stannous ion in the presence of glucarate (K. Y. Pak et al., Abstract No. 268 from the "Proceedings of the 36th Annual Meeting," *J. Nucl. Med.*, Vol. 30, No. 793 (1989); K. Y. Pak et al., *J. Nucl. Med.*, 33, 144 (1992); A. F. Verbruggen, *Eur. J. Nucl. Med.*, 17, 346 (1990)); stannous ion in the presence of benzoic acid derivatives (S. J. Mather et al., *J. Nucl. Med.*, 31, 692 (1990); U.S. Pat. No. 4,666,698 to Schwarz; PCT Publication No. 85/03231 to Institutt for Energiteknikk; and U.S. Pat. No. 5,164,175 to Bremer); stannous ion in the presence of diethylenetriaminepentaacetic acid derivatives (U.S. Pat. Nos. 4,668,503 and 4,479,930 to Hnatowich; U.S. Pat. No. 4,652,440 to Paik et al.; and U.S. Pat. No. 4,421,735 to Haber et al.); stannous ion in the presence of saccharic acid (U.S. Pat. No. 5,317,091 to Subramanian; WO 88/07382 to Centocor Cardiovascular Imaging Partners, L.P.;) stannous ion in the presence of glucoheptonate (U.S. Pat. No. 4,670,545 to Fritzberg et al.); stannous ion in the presence of D-gluconate (U.S. Pat. No. 5,225,180 to Dean et al.) have been used to effect technetium-99m labeling of sulfhydryl group-bearing peptides. In addition, dithionite has been used as the reducing agent for pertechnetate-99m (U.S. Pat. No. 4,647,445 to Lees).

The labeling of sulfhydryl group-bearing peptides using $^{99m}TcNCl_4^-$ has also been described (WO 87/04164 to the University of Melbourne).

There are several drawbacks associated with the above-mentioned processes for labeling sulfhydryl group-bearing biomolecules. First, because hydrochloric acid solutions of stannous ions are generally employed as vehicles for the pertechnetate-99m salt reducing agent, and such solutions are generally admixed with solutions of the biomolecules to be labeled, the hydrochloric acid can denature or otherwise chemically modify the biomolecule to be labeled, potentially rendering it inactive. On the other hand, basic neutralization of the stannous ion/hydrochloric acid solution prior to admixing with the solution of the biomolecule to be labeled can be problematic if the biomolecule to be labeled is particularly sensitive to base and also because such neutralization adds an extra step to the labeling process. Thus, there is a need for a method for labeling biomolecules with a radionuclide, preferably with a pertechnetate-99m salt, that excludes the use of either acidic or basic solutions.

In addition, solutions of biomolecule to be labeled, radionuclide and radionuclide reducing agent that additionally contain additives such as tartrate ion, glucarate, benzoic acid derivatives, benzoic acid derivatives, diethylenetriamine-pentaacetic acid derivatives, saccharic acid and D-gluconate can be expensive and/or time consuming to prepare. Thus, there is a need for a method of labeling biomolecules with a radionuclide, preferably with a pertechnetate-99m salt, that excludes the use of such additives.

Citation or identification of any reference in Section 2 of this application shall not be construed as an admission that such reference is available as prior art to the present invention.

3. SUMMARY OF THE INVENTION

The present invention is based on the surprising discovery that the labeling of sulfhydryl group-bearing biomolecules with a rhenium-186m or preferably a technetium-99m radionuclide, wherein the rhenium-186m is in the form of perrhenate-186m salt and technetium-99m is in the form of pertechnetate-99m salt, can occur when a source of stannous cation, wherein the stannous cation is in the form of a stannous salt, is premixed with a water-miscible organic solvent capable of at least partially, preferably completely, dissolving the stannous salt, prior to treatment with the biomolecule. This novel process of radionuclide labeling completely avoids the need for using acids, bases, or other additives that promote radionuclide-labeling of sulfhydryl groups or that necessitate neutralization of the biomolecule-radionuclide reaction mixture.

It is an object of the present invention to provide a method for labeling sulfhydryl group-bearing biomolecules with a radionuclide, wherein a stannous salt used to reduce the radionuclide is premixed with a water-miscible organic solvent. The radionuclide can be rhenium-186m, preferably in the form of perrhenate-186m salt, or the radionuclide can be technetium-99m, preferably in the form of pertechnetate-99m salt. In a preferred embodiment of the invention, the radionuclide is technetium-99m, in the form of a pertechnetate-99m salt.

Thus, it is an object of the present invention to provide a composition useful for the radionuclide labeling of a sulfhydryl group-bearing biomolecule, the composition prepared by a method comprising the steps of:
(a) admixing a mixture of a stannous salt and a water-miscible organic solvent with a buffer solution to afford a tin composition;
(b) admixing the tin composition with a sulfhydryl group-bearing biomolecule to afford a tin/biomolecule mixture; and
(c) lyophilizing the tin/biomolecule mixture, with the proviso that the stannous salt is not $Sn(OH)_2$.

In addition, the present invention provides for a method for labeling a sulfhydryl group-bearing biomolecule with a radionuclide, comprising the step of admixing the radionuclide with a composition prepared by a method comprising the steps of:
(a) admixing a mixture of a stannous salt and a water-miscible organic solvent with a buffer solution to afford a tin composition;
(b) admixing the tin composition with a sulfhydryl group-bearing biomolecule to afford a tin/biomolecule mixture; and
(c) lyophilizing the tin/biomolecule mixture, with the proviso that the stannous salt is not $Sn(OH)_2$.

In a preferred embodiment of the invention, the radionuclide technetium-99m, in the form of a pertechnetate-99m salt.

It is a further object of the present invention to provide a kit useful for the direct labeling of sulfhydryl group-bearing biomolecules, the kit comprising a composition prepared by a method comprising the steps of:
(a) admixing a mixture of a stannous salt and a water-miscible organic solvent with a buffer solution to afford a tin composition;
(b) admixing the tin composition with a sulfhydryl group-bearing biomolecule to afford a tin/biomolecule mixture; and
(c) lyophilizing the tin/biomolecule mixture, with the proviso that the stannous salt is not $Sn(OH)_2$.

It is a still further object of this invention to provide a method for imaging tissue of a mammal patient or subject, comprising administering to said patient or subject the product of admixing a radionuclide with a composition prepared by a method comprising the steps of:
(a) admixing a mixture of a stannous salt and a water-miscible organic solvent with a first buffer solution to afford a tin composition;
(b) admixing the tin composition with a sulfhydryl group-bearing biomolecule to afford a tin/biomolecule mixture; and
(c) lyophilizing the tin/biomolecule mixture, with the proviso that the stannous salt is not $Sn(OH)_2$.

In a preferred embodiment of the invention, the radionuclide is technetium-99m, in the form of a pertechnetate-99m salt.

As used herein, the term "buffer solution" means a sterile buffer solution having a physiological pH.

As used herein, the term "perrhenate-186 salt" is equivalent to $^{186m}ReO_4^-$.

As used herein, the term "pertechnetate-99m salt" is equivalent to $^{99m}TcO_4^-$.

As used herein, the term "biomolecule" refers to a whole molecule protein, protein fragment or a peptide, each comprising at least one sulfhydryl group.

As used herein, the term "radionuclide" includes technetium-99m and rhenium-186m.

As used herein, "HPLC" is high performance liquid chromatography.

As used herein, "PBS" is phosphate-buffered saline.

As used herein, the term "kit" refers to an assemblage of at least one vessel that comprises a biomolecule to be radiolabelled, wherein the biomolecule is either in lyophilized form or in solution.

The present invention may by more fully understood by reference to the following detailed description, illustrative examples of specific embodiments which are offered for purposes of illustration only and not by way of limitation.

5. DETAILED DESCRIPTION OF THE INVENTION

5.1 Technetium-99m Labeling of Protein Fragments

The radionuclide-labeling methods of the present invention are useful for the radionuclide labeling of biomolecules, particularly monoclonal or polyclonal antibody fragments, bearing sulfhydryl groups. However, other sulfhydryl group-bearing biomolecules, such as albumins, drugs, cytokines, enzymes, hormones, immune modulators, receptor proteins and the like, can also be labeled using the methods of the present invention.

It is to be understood that when the biomolecules to be labeled are antibody fragments, the antibody fragments can be those that bind to antigens which include, but are not limited to, antigens produced by or associated with tumors, infectious lesions, microorganisms, parasites, myocardial infarctions, clots, atherosclerotic plaque, or normal organs or tissues.

To increase the efficacy of a labeled antibody, while retaining its specificity to a desired target site, it may be desirable to digest whole molecule antibodies into those having Fab' chains. Typically, whole molecule antibodies are first digested into F(ab')$_2$ fragments, which are then digested into Fab' fragments. Reagents useful for digesting whole molecule antibodies into F(ab')$_2$ fragments include pepsin, papain and preferably, bromelain.

Solutions of whole molecule antibodies to be digested are prepared by dissolving the whole molecule antibody in a sterile buffer solution having a physiological pH. Examples of such buffer solutions include, but are not limited to phosphate buffers, acetate buffers, citrate buffers, Tris buffers, Tris EDTA buffers and the like. Preferably, the buffer solution is Tris EDTA buffer. Such solutions of whole molecule antibodies are advantageously stored at low temperatures, such as −78° C. to about 0° C., preferably at about −20° C., prior to use.

Where bromelain is used as the digestion agent, the bromelain is advantageously used in conjunction with cysteine, which functions to activate bromelain. In addition, quenching agents, such as N-ethylmaleimide, can be useful to preclude excessive digestion of the antibody molecules. Such methods of antibody digestion are well known to those skilled in the art (see, for example, Y. Hashimoto et al., *Radiology* 171: 223 (1989); and M. Mariani et al., Fifth Immunoconjugates in Cancer Book of Abstracts 191 (1992)).

The progress of such a digestion reaction can be monitored, for example using HPLC, by comparing molecular weight values of the desired antibody digestion products with known molecular weight standards. Solutions of the antibody digestion reaction mixture can be stored at about 0–10° C., preferably at about 4° C. if further purification of the antibody digestion reaction mixture will occur within 3 hours of quenching. If further purification of the antibody digestion reaction mixture will take place more than 3 hours subsequent to quenching, the reaction mixture can be frozen at about −78 to −10° C., preferably at about −20° C.

The digested antibody fragments are purified by methods known to those skilled in the art, such as column chromatography, preferably over sephacryl gel using PBS as an eluent. The resulting solutions of purified digested protein fragments are concentrated and stored as solids, typically at about −78° C. to about 0° C. If such F(ab')$_2$ fragments are to be later converted to Fab' fragments, the F(ab')$_2$ fragments are thawed from storage temperatures and warmed to a temperature of about 4° C. to about 37° C., preferably to room temperature, prior to use.

It is additionally useful for biomolecules that bear disulfide bonds, such as for example monoclonal or polyclonal antibodies, to be reduced such that at least one disulfide bond thereof is transformed into two sulfhydryl groups capable of bonding with technetium-99m. In this way, F(ab')$_2$ fragments having disulfide bonds are converted to Fab' fragments which bear sulfhydryl groups which can be readily radiolabelled according to the methods described herein. Reducing agents useful for reducing disulfide bonds to sulfhydryl groups include sodium borohydride, sodium phosphorothioate, 2,3-dihydroxybutane-1,4-dithiol, 2-aminoethanethiol HCl, 2-aminoethanol HCl, 2-mercaptoethylamine, thioglycolate, Sn(II), Co(I), Ti(II), dithiothreitol, cysteine, N-acetylcysteine, cyanide, glutathione, ascorbic acid, 2-mercaptoethanol, and other reducing agents, useful for reducing a disulfide bond to sulfhydryl groups, known to those skilled in the art. Preferably, the reducing agent useful for reducing disulfide bonds to sulfhydryl groups is 2-mercaptoethanol.

If 2-mercaptoethanol is used as the reducing agent, it is preferable that the 2-mercaptoethanol be used in an about 500 to about 2000 molar excess relative to the biomolecule having the disulfide bonds to be reduced, most preferably in an about 1000 molar excess relative to the biomolecule having the disulfide bonds to be reduced.

The resulting Fab' fragment is purified from the reducing agent using column chromatography or other conventional techniques useful for the purification of protein fragments. Columns useful for the purification of Fab' fragments are those containing sizing gels or resins including dextrans such as Sephadex G-10, G-25 or G-50 (Pharmacia, Piscataway, N.J.); Fractogel TSK HW55 (EM Science, Gibbstown, N.J.); polyacrylamides such as P-4, P-6 (BioRad, Richmond, Calif.), and the like. Preferably, the peptide fragment having sulfhydryl groups is purified via chromatography through a column which has been equilibrated with buffer solution, such as for example phosphate-buffered saline, and over sephacryl gel. If a Fab' fragment is to be purified via column chromatography, it is advantageous that the column contain approximately 1 mL of resin per mg of Fab' to be purified, with a minimum of 7 mL of resin for Fab' samples less that 7 mg.

Prior to bond formation with the radionuclide, the biomolecules bearing sulfhydryl groups, such as Fab' fragments, are admixed with tin, specifically stannous (Sn$^{2+}$) ion. The rhenium-186m or technetium-99m radionuclides are preferably employed as salts of perrhenate-186m or pertechnetate-99m, respectively. When present in the +7 oxidation state, e.g., in the form of perrhenate-186m ion, rhenium-186m is reduced by stannous ion to a form of rhenium-186m having a +3, +4 or +5 oxidation state and a form of rhenium-186m that is capable of forming a bond with a sulfhydryl group. Likewise, when present in the +7 oxidation state, e.g., in the form of pertechnetate-99m ion, technetium-99m is reduced by stannous ion to a form of technetium-99m having a +3, +4 or +5 oxidation state and a form of technetium-99m that is capable of forming a bond with a sulfhydryl group.

The stannous ion can be in the form of any reasonably stable stannous salt, such as for example stannous chloride, stannous iodide, stannous bromide, stannous fluoride, stannous acetate, and the like, such that the stannous salt is at least partially, preferably fully, soluble in a water-miscible organic solvent. Preferably, the stannous salt is stannous chloride. The stannous salt, however, cannot be stannous hydroxide (Sn(OH)$_2$). This is because Sn(OH)$_2$ forms colloids with water and can itself be labeled with radionuclide. In this way, Sn(OH)$_2$ can disadvantageously compete with the biomolecule for radionuclide.

Prior to reaction with the radionuclide, the stannous salt is admixed with a water-miscible organic solvent. The stannous salt must be at least partially soluble in the water-miscible organic solvent. The water-miscible organic solvent must be capable of at least partially dissolving the stannous salt and evaporating under reduced pressure. Suitable water-miscible organic solvents include, but are not limited to methanol, ethanol, n-propanol, iso-propanol, iso-butanol, sec-butanol, dimethylsulfoxide, dimethylformamide, N-methylpyrrolidinone, other water-miscible organic solvents known to those skilled in the art that are capable of at least partially dissolving the stannous salt and that do not react with sulfhydryl groups when admixed with water at room temperature, and mixtures thereof. Preferably, the water-miscible organic solvent is ethanol.

Because it is possible that a particular stannous salt capable of reducing the radionuclide to the +3, +4 or +5 oxidation state may not be at least partially soluble in one of the water-miscible organic solvents described above, it is well within the purview of one of ordinary skill in the art to select from the above list of water-miscible organic solvents a particular water-miscible organic solvent capable of at least partially dissolving a particular stannous salt.

It is important that the water-miscible organic solvent be substantially free of water at the time it is admixed with the stannous salt. By "substantially free of water" is meant that the water-miscible organic solvent is at least 96%, preferably at least 99%, and most preferably at least 99.99% free of water. The water-miscible organic solvents useful in this regard can be commercially purchased in their anhydrous state, purified using methods described in Purification of Laboratory Chemicals, D. D. Perrin et al., Third Edition, Pergamon Press, Oxford, 1988, or purified using other methods known to those skilled in the art.

Prior to admixture with the sulfhydryl group-bearing biomolecule to be labeled, the mixture of water-miscible organic solvent and stannous salt is diluted with an aqueous buffer solution to provide a tin composition. It is important that the water-miscible organic solvent and stannous salt be admixed prior to admixture with the aqueous buffer solution. Without being bound to any particular theory, it is believed that the water-miscible organic solvent coordinates with stannous ions, via complexation of lone pairs of electrons residing on oxygen or nitrogen atoms of water-miscible organic solvent molecules. It is believed that such coordination protects the stannous ion from water-mediated oxidation which could interfere with the stannous ions' ability to reduce the chosen radionuclide and possibly render it incapable of bonding with the biomolecule. Accordingly, the water-miscible organic solvent that is admixed with the stannous salt must be anhydrous, so as to maximize the protective benefit of the coordinating water-miscible organic solvent.

Buffer solutions useful for forming the tin compositions are aqueous, and include phosphate buffers, acetate buffers, isotonic saline, citrate buffers, Tris buffers, Tris EDTA buffers and the like. Preferably, the buffer solution is PBS. The aqueous buffer solution should be purged with an inert gas, such as nitrogen or argon, prior to dilution of the water-miscible organic solvent and stannous salt mixture, so as to rid the buffer solution of amounts of oxygen gas dissolved therein. The presence of such oxygen gas could promote oxidation of free sulfhydryl groups on the biomolecule to be labeled.

It is to be pointed out that over time, the tin composition forms tin colloids. This is undesirable, because such tin colloids can be present in the product of lyophilization described below, and compete with the sulfhydryl group(s) for radionuclide bonding. Accordingly, to limit the formation of tin colloids, the tin composition should be lyophilized within 120 hours, preferably within 48 hours, of preparation.

The mixture of buffer solution, stannous salt and water-miscible organic solvent, i.e., the tin composition, is admixed with the sulfhydryl group-bearing biomolecule to be labeled to provide an aqueous tin/biomolecule mixture. Optionally, the sulfhydryl group-bearing biomolecule to be labeled is diluted with buffer solution, preferably PBS, prior to admixture with the tin composition. Where the sulfhydryl group-bearing biomolecule to be labeled is diluted with buffer solution prior to admixture with the tin composition, the buffer solution containing the sulfhydryl group-bearing biomolecule is purged with an inert gas, such as nitrogen or argon, so as to rid the buffer solution of amounts of oxygen gas dissolved therein. This is done to minimize the likelihood of oxidation of free sulfhydryl groups on the biomolecule to be labeled.

Without being bound to any particular theory, it is believed that upon admixture of the tin composition with the biomolecule to be labeled, water that forms hydrogen bonds with the sulfhydryl groups of the biomolecule is displaced by the water-miscible organic solvent of the tin complex, allowing interaction between the sulfhydryl groups and the stannous ions. It is to be pointed out that the source of the "water" is either the tin composition itself or buffer solution with which the biomolecule is admixed, prior to admixture with the biomolecule.

In addition, it is believed that the water-miscible organic solvent of the tin composition can seek hydrophobic domains of the biomolecule, in particular hydrophobic domains of a concave face thereof, thereby "opening" the hydrophobic domains and facilitating exposure of sulfhydryl groups therein to stannous ion.

Following admixture of the sulfhydryl group-bearing biomolecule and the tin composition, the resulting aqueous tin/biomolecule mixture is allowed to incubate at from about −20° C. to about 50° C., preferably from about 0° C. to about 10° C., and most preferably at about 4° C. for about 1 hour to about 10 days, preferably from about 1 to about 3 days. Not to be bound by any particular theory, it is believed that incubation of the stannous salt and sulfhydryl group-bearing protein fragment gives rise to a tin:biomolecule complex that is solvated by the water-miscible organic solvent.

Following incubation, the aqueous tin/biomolecule mixture is lyophilized. Without being bound to any particular theory, it is believed that lyophilization of the aqueous tin/biomolecule mixture facilitates formation of a relatively stable tin:biomolecule complex that is free from solvent, including water. Accordingly, it is believed that the product of lyophilization is a tin:biomolecule complex. It is further believed that in the tin:biomolecule complex, stannous ion coordinates with biomolecule sulfhydryl groups. By virtue of the lyophilization step, the tin:biomolecule complex is "frozen" into a configuration which is not characteristic of its native configuration, i.e., its configuration assumed in a normal, physiological environment. In addition, it is believed that the coordination of stannous ion to biomolecule sulfhydryl groups protects the sulfhydryl groups from oxidation during and following lyophilization.

Lyophilization will also facilitate storage and increase shelf life of the product. Optionally, prior to lyophilization, stabilizing agents such as about 0.1% to about 5.0%, preferably 0.5% aqueous sucrose; and about 0.1 M to about 1.0 M, preferably 0.4 M glycine, mannitol, trehalose, lactose, glucose or mixtures thereof, can be added to the aqueous tin/biomolecule mixture to further prolong the shelf life of the product. It is to be understood that because lyophilization is generally performed under reduced pressure, lyophilization of the aqueous tin/biomolecule mixture removes the water-miscible organic solvent and the water component of the buffer solution.

In addition, the aqueous tin/biomolecule mixture is optionally filtered prior to lyophilization. This filtration step can be used, in accordance with good manufacturing practices, to remove unwanted material, such as bacteria or other particulate contaminants, from the tin/biomolecule mixture. If the aqueous tin/biomolecule mixture is filtered prior to lyophilization, the pore size of the filter should be 0.22 µm or less.

If, following lyophilization and labeling with radionuclide, the resulting labeled biomolecule is to be administered to a mammal, preferably human, subject, the present methods must be performed under sterile conditions, in accordance with good manufacturing practices.

Lyophilization of the aqueous tin/biomolecule mixture is performed using standard lyophilization techniques. Advantageously, the aqueous tin/biomolecule mixture is placed in a suitable vessel, such as a vial, frozen at a temperature of −40° C. or colder, and subjected to reduced pressure, preferably 50 µm or less, most preferably 10 µm or less, until lyophilization is complete, i.e., until the mixture visually appears to be completely dry. At the above-mentioned temperature and pressure ranges, lyophilization is generally complete within 48 hours.

The product of lyophilization can be stored in its lyophilization vessel until radionuclide labeling is desired. Preferably, the product of lyophilization is sealed in its lyophilization vessel under vacuum or under a blanket of inert gas such as nitrogen or argon. If long-term, i.e., several-year, storage of the product of lyophilization is desired, the vessel containing the product of lyophilization is preferably stored in a dark environment, at room temperature or cooler. Preferably, the storage temperature is between about −78° C. and about 15° C., most preferably between about −10° C. and 15° C. If the product of lyophilization is stored in a dark environment under vacuum and at a temperature of 2–8° C., the product of lyophilization is stable for several years.

The product of lyophilization is treated with a radionuclide so as to effect labeling of the sulfhydryl group-bearing biomolecule. Useful forms of radionuclide include salts of pertechnetate-99m and perrhenate-186m. Sodium pertechnetate-99m, can be obtained from a conventional $^{99m}Tc/^{99}Mo$ generator as a solution in isotonic saline. Such a $^{99m}Tc/^{99}Mo$ generator is obtainable commercially from, for example, Mallinckrodt Medical Inc., St. Louis, Mo. It is to be understood that sodium perrhenate-186m can be obtained from a generator analogous to that used for the production of sodium pertechnetate-99m. For efficient labeling, the mCi of radionuclide per mg of sulfhydryl group-bearing biomolecule to be labeled should be greater than 20 mCi/mg and less than 50 mCi/mg.

The radionuclide used in the present labeling method is advantageously used as an aqueous solution. Without being bound by any particular theory, it is believed that the abnormal configuration assumed by the tin:biomolecule upon being "frozen" during lyophilization becomes restored upon admixture with the radionuclide solution, but not before the radionuclide is reduced by the stannous ion and subsequently bonded to a sulfhydryl group of the biomolecule. In addition, it is believed that because the stannous ion is coordinated to the biomolecule sulfhydryl groups in the product of lyophilization, the rate of radionuclide labeling significantly exceeds that of diffusion since the radionuclide, once reduced, is already in close proximity of the sulfhydryl group, and is capable of quickly reacting therewith.

Useful aqueous solvents include, but are not limited to, phosphate buffer, acetate buffer, isotonic saline, citrate buffer, Tris buffer, Tris EDTA buffer, and the like. Preferably, the aqueous solvent is isotonic saline. Advantageously, the radionuclide is used as an isotonic saline solution obtained directly from a pertechnetate-99m or perrhenate-186 generator. It is to be pointed out that aqueous solvent is necessary for the labeling reaction of biomolecule with radionuclide.

If the product of lyophilization had been stored at a temperature that is below room temperature, the product of lyophilization should be allowed to warm to room temperature prior to admixture with the radionuclide solution.

If the resulting radionuclide-labeled biomolecule is to be administered to a mammal, preferably human, patient or subject, it is advantageous to admix the product of lyophilization with radionuclide either by syringe addition of an aqueous solution of radionuclide to the product of lyophilization.

Following admixture of the product of lyophilization with radionuclide, the resulting mixture is allowed to incubate at from about room temperature to about 37° C., preferably at room temperature, for about one minute to one hour, preferably for about 15 minutes. Such incubation facilitates radionuclide labeling of the sulfhydryl group-bearing biomolecule.

The resulting radionuclide-labeled biomolecules are suitable for use in scintigraphic imaging of, e.g., tumors, infectious lesions, microorganisms, blood clots, myocardial infarctions, atherosclerotic plaque or normal organs and tissues. Such imaging methods are well-known in the art.

If the resulting radionuclide-labeled biomolecule is to be directly administered to a mammal, preferably human, subject or patient, the solution can optionally be filtered prior to administration. Such a filter should have a pore size of 0.22 μm or less.

In an alternate embodiment of the invention, the aqueous tin/biomolecule mixture is not lyophilized and instead, the aqueous tin/biomolecule mixture is directly admixed with the radionuclide solution to effect biomolecule labeling. The aqueous tin/biomolecule mixture can be added to the radionuclide solution, or vice versa.

4.2 Kit for Technetium-99m Labeling of Sulfhydryl Group-Bearing Protein Fragments Another embodiment of the present invention relates to a kit useful for the direct labeling of sulfhydryl group-bearing biomolecules. The kit can further comprise other kit components such as one or more filters, vials, syringes, syringe needles, direction for use, or other kit components known to those skilled in the art.

Such a kit is useful as a convenient means for the radionuclide labeling of sulfhydryl group-bearing biomolecules in, for example, a medical care facility or a research laboratory.

The kit of the present invention comprises a novel composition useful for the direct labeling of a sulfhydryl group-bearing biomolecule, the composition prepared by a method comprising the steps of:

(a) admixing a mixture of a stannous salt and a water-miscible organic solvent with a buffer solution to afford a tin composition;

(b) admixing the tin composition with a sulfhydryl group-bearing biomolecule to afford a tin/biomolecule mixture; and (c) lyophilizing the tin/biomolecule mixture, with the proviso that the stannous salt is not $Sn(OH)_2$.

Details of the preparation of the composition useful for the radionuclide labeling of sulfhydryl group-bearing biomolecules are recited in Section 5.1, above.

Preferably, the biomolecule used to prepare the composition of the kit is an antibody fragment which, when radiolabelled and subsequently administered to a mammal, preferably human, patient or subject, binds to an antigen produced by or associated with an organ or tissue in normal or abnormal condition, allowing the detection of the organ or tissue by the use of an external imaging camera.

Advantageously, the composition of the kit is stored in a suitable container, e.g., a vial, such that the container is large enough to accommodate a volume of radionuclide solution which can be added to the container to facilitate labeling of the sulfhydryl group-bearing biomolecule. Preferably, the radionuclide is added to the container containing the composition, i.e., the product of lyophilization, as a buffer solution of radionuclide, wherein the radionuclide is preferably in the form of sodium pertechnetate-99m, and the buffer solution is a phosphate buffer, acetate buffer, citrate buffer, isotonic saline, Tris buffer, Tris EDTA buffer, or the like. Preferably, the buffer solution is isotonic saline.

The container is preferably a sterile vial, fitted with a rubber septum, so as to allow introduction of radionuclide solution via syringe needle while minimizing the risk of contamination of the composition. The composition contained within the container can optionally be sealed under vacuum, or under a blanket of inert gas, such as nitrogen or argon.

It will be understood that the radionuclide used to label the composition of the kit can be obtained, preferably in the form of sodium pertechnetate-99m or sodium perrhenate-186m solutions, using radionuclide generators as described in Section 5.1, above. Accordingly, it is advantageous to have such a radionuclide generator within the same facility as that in which the kit is used.

If, following the admixture of radionuclide solution with the composition of the kit, the mixture containing radiolabelled biomolecule is to be administered to a mammal, preferably human, subject or patient, it may be advantageous to filter that mixture, so as to ensure the removal of any bacterial contaminants therefrom, and to act in accordance with good manufacturing practices. In such a case, the kit of the present invention can include a filters, having a pore size of no greater than 22 μm, useful for this purpose.

The composition of the present kit typically comprises about 0.01–10 mg, preferably about 0.5–2 mg, per unit dose of a sulfhydryl group-bearing biomolecule, preferably in the form of an antibody fragment, which specifically binds to an antigen.

Variations and modifications of these kits will be readily apparent to the ordinary skilled artisan, as a function of the individual needs of the patient or treatment regimen, as well as of variations in the form in which the radionuclides may become available.

4.3 Scintigraphic Imaging Using Radiolabelled Biomolecules

Radionuclide-labeled biomolecules, especially antibodies and antibody fragments, prepared according to the methods of the invention, will be suitable, and in fact particularly convenient and efficacious, in methods of non-invasive scintigraphic imaging. In particular, in a method imaging a tumor, a deep venous thrombosis, a left atrial thrombus, a pulmonary embolism, an infectious lesion, a myocardial infarction, a blood clot such as a deep venous thrombosis, an atrial thrombus or a pulmonary embolism, atherosclerotic plaque, or a normal organ or tissue, wherein an antibody or antibody fragment which specifically binds to an antigen produced by or associated with said tumor, deep venous thrombosis, left atrial thrombus, pulmonary embolism, infectious lesion, myocardial infarction, blood clot such as a deep venous thrombosis, an atrial thrombus or a pulmonary embolism, atherosclerotic plaque, or normal organ or tissue, and labeled with technetium-99m capable of external detection, is parenterally or intravenously injected into a mammal, preferably human, patient or subject and, after a sufficient time for the labeled antibody or antibody fragment to localize and for non-target background to clear, the site or sites of accretion of the labeled antibody or antibody fragment are detected by an external imaging camera, it will be an improvement to use a Tc-99m-labeled antibody or antibody fragment made according to the method of the present invention. Such imaging methods are well known in the art.

4.4 In Vitro Applications of Radiolabelled Biomolecules

In addition to being useful for scintigraphic imaging in vivo, radiolabelled biomolecules can be used in various in vitro applications. For example, when the biomolecule to be labeled is antibody or fragment thereof, the antibody or antibody fragment can be labeled by the present methods and used for radio immunoassays or affinity measurements, e.g., admixing the labeled antibody or fragment thereof with a mixture of antigens, thereby allowing the antigen(s) specific to the labeled antibody or antibody fragment to be readily detected, quantified, and subsequently purified. Such immunoassays and affinity measurements are capable of being performed using relatively small amounts of both antigen and antibody. In addition, labeled biomolecules, by virtue of the fact that they bind to specific antigens, are useful for the identification and characterization of general laboratory materials and analytes, e.g., protein and/or peptide reagents, biological probes, and the like.

The following series of examples are presented by way of illustration and not by way of limitation on the scope of the invention.

6. EXAMPLE: DIRECT LABELING OF MH1-FAB' ANTIFIBRIN MURINE MONOCLONAL ANTIBODY FRAGMENT

6.1 Materials and Methods

Tris EDTA buffer was used as a mixture of 50 mM Tris and 2 mM EDTA, the pH of the Tris EDTA buffer being 7.0. PBS buffer was used as a mixture of 1.66 mM $NaH_2PO_4$, 8 mM $Na_2HPO_4$, and 150 mM NaCl, the pH of the PBS buffer being 7.4. A stock solution of bromelain was prepared by adding 20 units/mL of bromelain solution to 10 mL Tris EDTA buffer (pH 7.0), agitating the mixture by end-over-end inversion for 5 (±1) minutes, centrifuging 1 mL of the resulting suspension for 5 (±1) minutes, decanting and saving the supernatant, adding 100 μL of the supernatant to 900 μL of fresh Tris EDTA and measuring the optical density of the resulting solution at 280 nm, making sure that the optical density was between 1.1 and 1.3. A stock solution of cysteine (100 mM in Tris EDTA buffer (pH 7.0)) was prepared by adding 121.2 mg of cysteine to 10 mL of Tris EDTA and storing the resulting solution at room temperature.

$F(ab')_2$ Fragments: A stock solution of N-ethylmaleimide (100 mM in Tris EDTA buffer) was prepared by dissolving 125 mg of N-ethylmaleimide in 10 mL of Tris EDTA, wrapping the vessel containing the N-ethylmaleimide solution in aluminum foil, allowing the solution to stand for 10 minutes at room temperature and mixing its contents by end-over-end rotation just prior to use. All reagents were pre-warmed to a temperature of 37° C. prior to use.

Fab' Fragments: A stock solution of stannous chloride/anhydrous ethanol solution was prepared by dissolving 12.5 mg of stannous chloride in 2.0 mL of absolute (200 proof) ethanol and mixing and incubating the stock solution at room temperature.

High-performance liquid chromatography was performed on a Waters 501 HPLC equipped with a BioSil SEC 250 gel filtration column. 2-Mercaptoethanol was used as a concentrated solution (14 M) purchased from Sigma Chemical Co., St. Louis, Mo. Bromelain was purchased from Calbiochem, San Diego, Calif.; anhydrous ethanol was purchased from Quantum Chemical Corp., Tuscola, Ill.; $N_2$ was medical grade, i.e., $O_2$-free, and was obtained from Mittler Supply Co., South Bend, Ind.

6.2 Proteolytic Digestion of Whole Molecule Antifibrin Monoclonal Antibody MH1 to MH1-F(ab')$_2$ 4 mL of 10 mg/mL whole molecule antifibrin MH1 monoclonal antibody in Tris EDTA were placed into a 5 mL tube fitted with a screw cap. 0.8 mL of bromelain stock solution, providing 0.4 units of bromelain per mg. of antibody, were added to the MH1 solution, and the tube was inverted twice, end-over-end. 40 μL of cysteine stock solution, providing a total concentration of 1 mM cysteine, were added to the tube, and the tube was inverted twice, end-over-end. The tube was placed on a Cole Palmer Roto-Torque rotating tube holder placed in a warmbox, pre-equilibrated at 37° C.

The tube containing the digested mixture was rotated in the warmbox at a rate of 10 (±2) revolutions per minute. At 15 minute intervals, 20 μL aliquots of the reaction mixture were removed and to these aliquots were added 2 μL of N-ethylmaleimide stock solution to stop digestion. These samples of quenched reaction mixture were analyzed by HPLC for MH1-F(ab')$_2$ product, which showed a molecular weight of 110,000 when compared to molecular weight standards. When the last chromatogram indicated at least 70% digestion (generally between 20 and 45 minutes), full digestion was assumed. The reaction mixture was quenched via the addition of 0.4 mL of the N-ethylmaleimide stock solution, resulting in a 10 mM final concentration of N-methylmaleimide, and stored a temperature of between –20° C. and 4° C. prior to purification.

The resulting solution of MH1-F(ab')$_2$ was purified over a sephacryl Pharmacia S-200 HR filtration column which had been depyrogenated by passing filtered and degassed 0.5 M NaOH therethrough for 30 minutes and then equilibrated with PBS, and concentrated with an Amicon Centripep 30 Concentrator.

6.3 Reduction of MH1-F(ab')$_2$ to MH1-Fab'

Prior to reduction of the MH1-F(ab')$_2$ fragment obtained from Section 6.2, a Waters 486 HPLC and sephacryl S-300 gel filtration column, containing approximately 1 mg of resin per mg of MH1-Fab' to be purified, were pre-equilibrated with PBS as the mobile phase buffer. The column was then depyrogenated by passing 0.5 M NaOH (filtered and degassed) through it for 30 minutes at a flow rate of 0.5 mL/min. The column was then re-equilibrated with low endotoxin PBS at 1.0–2.0 mL/min for 30 (±5) minutes. Washing continued until the pH of the eluent was 7.3–7.5.

A 2 mL aliquot of 10 mg/mL of the MH1-F(ab')$_2$ fragment obtained from Section 6.2 in Tris EDTA buffer was added to a sealable, 5 mL depyrogenated reaction vessel. To the reaction vessel was added, under stirring with a magnetic stir bar, 14.3 μL of 2-mercaptoethanol, such that the 2-mercaptoethanol was in a roughly 1000 molar excess, relative to the MH1-F(ab')$_2$ fragment. Stirring proceeded for 1 minute (±5 seconds) and the mixture was incubated for 30 (±1) minutes at room temperature with gentle mixing (end-over-end inversion) every two minutes. After 30 (±1) minutes, the resulting MH1-Fab' fragment was separated from the 2-mercaptoethanol via purification over a sephacryl S-300 gel filtration column that was previously equilibrated with PBS buffer (pH 7.4). Purified MH1-Fab' fragment was collected into a tube into which a slow stream of nitrogen gas was flowing. The nitrogen flow continued following collection of purified Fab'. Typically, 300 μL of Fab' solution was removed for purity and concentration determination. The purity was determined by HPLC measurements on a BioRad SEC-250 size exclusion column, and by measuring the concentration of residual 2-mercaptoethanol using Ellman's reagent (G. F. Bickerstaff et al., *Anal. Biochem.* 210: 155–158 (1993)). The concentration of collected Fab' was determined spectroscopically ($\lambda$=280 nm; $\epsilon$=1.3 mL/mg cm).

6.4 Formation of MH1-Fab'-Tin Mixture 0.277 mL of SnCl$_2$/anhydrous ethanol solution (6.25 mg of SnCl$_2$/mL of anhydrous ethanol) were added to 18.9 mL of nitrogen-deaerated PBS. The resulting mixture of SnCl$_2$, ethanol and PBS was added to 3.9 mL of a solution of the MH1-Fab' fragment obtained above in Section 6.3 in PBS buffer, having a concentration of 2.96 mg/mL and being continuously degassed with nitrogen. The degassing was discontinued and the resulting mixture was allowed to stand in a closed, screw-capped test tube for 30 minutes at room temperature and stored at 2–8° C. for 48 (±1) hours. Immediately prior to lyophilization, the solution was filtered through a 0.22 μm Millex GV filter under a laminar flow hood. The filtered solution was transferred, in 1 mL aliquots, to twenty three 5 mL vials.

The aliquots were lyophilized in the vials by freezing on shelves pre-cooled to –40° C. or colder, applying a vacuum of 10 μm or less, and maintaining the solution at a temperature of –40° C. for at least 28 hours and until the solution was completely lyophilized. The lyophilized material was slowly warmed to 10° C. and sealed under vacuum. The vials containing the lyophilized material were fitted with rubber septa, sealed under vacuum and stored in a dark environment at 2–8° C.

6.5 Labeling Product of Lyophilization with Technetium-99m

A vial from Section 6.4 above, containing lyophilized material and being stored in a dark environment at 4° C. was allowed to warm to room temperature and was placed behind a lead shield. The rubber septum fitted onto the vial was cleaned with an alcohol swab. To the vial, which contained 0.5 mg of the product of lyophilization obtained as described in Section 6.4 above, was added 2.0 mL (12 mCi, ±2 mCi) of sodium pertechnetate-99m solution in preservative-free isotonic saline at room temperature via syringe. The vial was gently swirled for approximately 15 seconds to wet all internal vial surfaces. The resulting mixture was allowed to incubate at room temperature for 15 minutes. The resulting solution of technetium-99m-labeled MH1-Fab' fragment had a pH of 7.1 and a labeling efficiency of 98%, as determined by instant thin-layer chromatography, using 10% trichloroacetic acid in PBS as the eluent, wherein the labeling efficiency=$(\mu Ci_{origin})/(\mu Ci_{origin}+\mu Ci_{solvent\ front})$. The resulting solution was withdrawn from the vial into a syringe using a 10 mL syringe attached to an 0.22 μm Millex-GV filter and a 20 gauge needle. The needle and filter were removed, and the filtered solution of technetium-99m-labeled MH1-Fab' fragment was discharged into a clean glass vial.

7. EXAMPLE: DIRECT LABELING OF FAB' FRAGMENTS OF MONOCLONAL ANTIBODIES

The radiolabeling method disclosed in Section 6, above, was successfully used to label Fab' fragments of antifibrinogen (45J (ATCC HB 9740)), antiarsenic (ARS1) and antifibrin (MH1 (ATCC HB 9739)); as well as whole molecule anti-*Corneybacterium matrouchi* (CMAT1).

8. EXAMPLE: IMAGING OF PULMONARY EMBOLISM WITH TECHNETIUM-99M-LABELED MH1 ANTIFIBRIN ANTIBODY IN A HUMAN PATIENT

The technetium-99m labeled MH1 antifibrin antibody obtained from Section 6.5, above, was intravenously injected into a human patient who presented to an emergency room with symptoms of pulmonary embolism. A ventilation-perfusion scan was performed which was interpreted as being high probability for pulmonary embolism. The antifibrin antibody was injected intravenously via the patient's arm. The data and time of antibody injection, the labeling efficiency and the injected activity were all recorded.

An intravenous line was placed in the patient's arm vein. The line was continuously flushed (i.e., a saline solution at a rate of 5 cc/min) after antifibrin antibody injection. Prior to administration of the labeled antibody, preinjection bloods were drawn for measurement of human antimouse antibody titers, and hematologic and biochemical profiles. A baseline sample used to monitor blood clearances of the injected antibody was obtained. A urine specimen from the patient was obtained for analysis. Approximately 3 minutes after antibody injection, the first set of planar images was acquired. Additional images were acquired at 30 minutes, one hour, and two hours following antibody injection. Planar imaging was performed with a modern, large field of view gamma camera. The camera was equipped with a low energy, all-purpose Collimator. The 140 KeV photo peak of technetium-99m was used with a 20% symmetric window. The camera details were recorded. The imaging time and counts per view were recorded. Planar images consisted of 4 views which were acquired for at least 5 minutes per view. The patient was started on intravenous heparin, and a Doppler ultrasound was performed for diagnosis of deep vein thrombosis ("DVT"). The ultrasound was negative for DVT.

Figure 1:
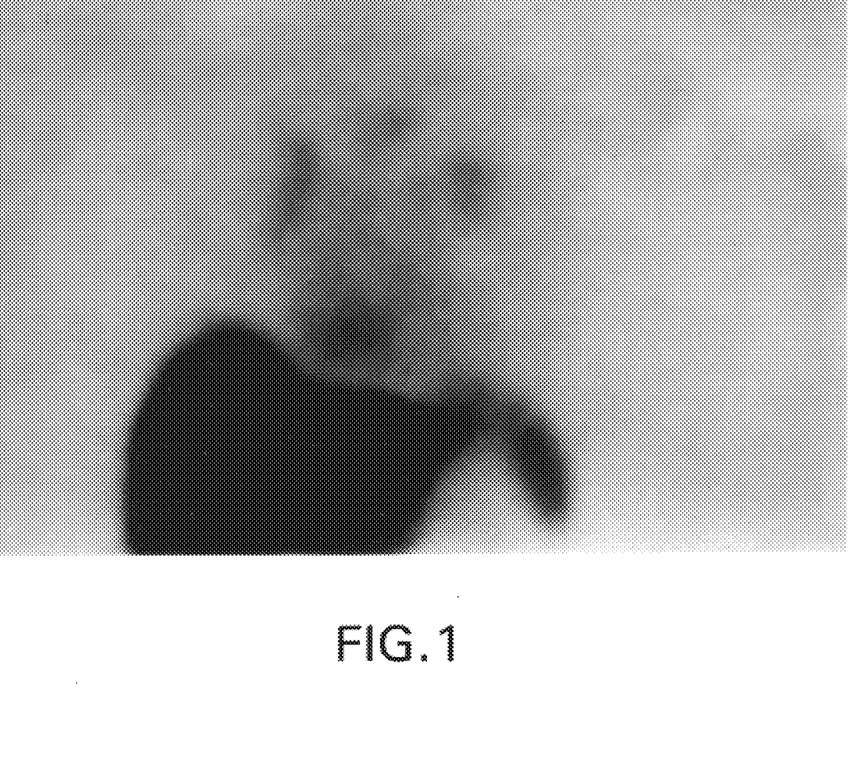
FIG. 1 is a photograph of a scintigraphic image confirming pulmonary embolism, i.e., a blood clot, in the anterior chest of a patient adminsitered with a technetium-99m-labeled MH-1 Fab' antifibrin agent.

Twenty-four hours following admission to the emergency room, a technetium-99m-labeled MH1 Fab' antifibrin antibody scan, performed 2 hours post-administration of the technetium-99m-labeled MH1 Fab' antifibrin agent, showed prominent uptake of the technetium-99m-labeled MH1 Fab' antifibrin antibody in the pulmonary arteries, clearly indicating the presence of blood clots (FIG. 1). The presence of these clots was further confirmed by contrast enhanced spiral computed tomography.

9. EXAMPLE: IMAGING OF A DEEP VEIN THROMBOSIS IN HUMAN PATIENTS

The Fab' fragment of the MH-1 antibody was directly labeled with sodium pertechnetate-99m according to the procedure disclosed in Section 6, above. The labeling occurred within 3 minutes with a high labeling efficiency of 96±4%. Specific activity in excess of 100 mCi/mg of antibody fragment was obtained and administered to patients with suspected acute deep venous thrombosis ("DVT"). Fifteen patients with a diagnosis of DVT were studied. Ten patients had lower extremity acute DVT, and five patients had upper extremity acute DVT, documented by contrast venogram in fifteen patients and/or doppler in nine patients. Anterior and posterior whole body images were obtained at 5–15 minutes, 60–90 minutes, 3–6 hours, and/or 24 hours following iv injection of the technetium-99m-labeled MH1 antibody fragment. No adverse events nor alteration in hematology, chemistry, or coagulation studies were noted. No patient developed an antibody response in 28 day follow up against MH-1. Blood clearance T1/2 of 2 hours with 6±3% activity in the blood at 24 hours. Images were evaluated without any clinical information by two observers to ascertain presence of potential thrombi and their location. Technetium-99m-labeled MH1 identified ten out of ten patients having lower extremity acute DVT, and five out of five patients having upper extremity acute DVT. In four of the patients, the MH-1 Fab' images detected additional lesions. However, in four patients having bilateral disease (two in each group), contralateral lesions were missed. One patient had a positive MH1 and venogram, and a negative doppler study. Early post injection images were very helpful for interpretation, and a second set of images were obtained at 3–6 hours following the injection. No additional information was obtained beyond the 6 hour image.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those described herein will become apparent to those skilled in the art and are intended to fall within the appended claims.

A number of references have been cited and the entire disclosures of which are incorporated herein by reference.

What is claimed is:

1. A composition prepared by a method comprising the steps of:
   (a) admixing a mixture of a stannous salt and a water-miscible organic solvent with a buffer solution to afford a tin composition;
   (b) admixing the tin composition with a sulfhydryl group-bearing biomolecule to afford a tin/biomolecule mixture; and
   (c) lyophilizing the tin/biomolecule mixture, with the proviso that the stannous salt is not $Sn(OH)_2$.

2. The composition of claim 1, wherein said water-miscible organic solvent is selected from the group consisting of methanol, ethanol, n-propanol, iso-propanol, isobutanol, sec-butanol, dimethylsulfoxide, dimethylformamide, and N-methylpyrrolidinone.

3. The composition of claim 2, wherein said water-miscible organic solvent is ethanol.

4. The composition of claim 1, wherein said stannous salt is selected from the group consisting of stannous chloride, stannous iodide, stannous bromide, stannous fluoride and stannous acetate.

5. The composition of claim 4, wherein said stannous salt is stannous chloride.

6. The composition of claim 1, wherein said buffer solution is selected from the group consisting of phosphate buffer, acetate buffer, isotonic saline, citrate buffer, Tris buffer and Tris EDTA buffer.

7. The composition of claim 6, wherein said buffer solution is phosphate-buffered saline.

8. The composition of claim 1, wherein the biomolecule is selected from the group consisting of a whole molecule protein, a protein fragment and a peptide.

9. The composition of claim 8, wherein the biomolecule is a monoclonal or polyclonal antibody.

10. A method for labeling a sulfhydryl group-bearing biomolecule with a radionuclide, comprising the step of admixing the radionuclide with a composition prepared by a method comprising the steps of:
    (a) admixing a mixture of a stannous salt and a water-miscible organic solvent with a first buffer solution to afford a tin composition;
    (b) admixing the tin composition with a sulfhydryl group-bearing biomolecule to afford a tin/biomolecule mixture; and
    (c) lyophilizing the tin/biomolecule mixture, with the proviso that the stannous salt is not $Sn(OH)_2$.

11. The method of claim 10, wherein the radionuclide is dissolved in a second buffer solution.

12. The method of claim 11, wherein said second buffer solution is selected from the group consisting of phosphate buffer, acetate buffer, isotonic saline, citrate buffer, Tris buffer and Tris EDTA buffer.

13. The method of claim 12, wherein said second buffer solution is isotonic saline.

14. The method of claim 10, wherein said water-miscible organic solvent is selected from the group consisting of methanol, ethanol, n-propanol, iso-propanol, isobutanol, sec-butanol, dimethylsulfoxide, dimethylformamide, and N-methylpyrrolidinone.

15. The method of claim 14, wherein said water-miscible organic solvent is ethanol.

16. The method of claim 10, wherein said stannous salt is selected from the group consisting of stannous chloride, stannous iodide, stannous bromide, stannous fluoride and stannous acetate.

17. The method of claim 16, wherein said stannous salt is stannous chloride.

18. The method of claim 10, wherein said first buffer solution is selected from the group consisting of phosphate buffer, acetate buffer, isotonic saline, citrate buffer, Tris buffer and Tris EDTA buffer.

19. The method of claim 18, wherein said first buffer solution is phosphate-buffered saline.

20. The method of claim 10, wherein the radionuclide is selected from the group consisting of technetium-99m and rhenium-186m.

21. The method of claim 20, wherein the technetium-99m is in the form of a salt of pertechnetate-99m.

22. The method of claim 20, wherein the rhenium-186m is in the form of a salt of perrhenate-186m.

23. A kit comprising a container comprising a composition prepared by a method comprising the steps of:
   (a) admixing a mixture of a stannous salt and a water-miscible organic solvent with a buffer solution to afford a tin composition;
   (b) admixing the tin composition with a sulfhydryl group-bearing biomolecule to afford a tin/biomolecule mixture; and
   (c) lyophilizing the tin/biomolecule mixture, with the proviso that the stannous salt is not $Sn(OH)_2$.

24. The kit of claim 23, wherein said water-miscible organic solvent is selected from the group consisting of methanol, ethanol, n-propanol, iso-propanol, isobutanol, sec-butanol, dimethylsulfoxide, dimethylformamide, and N-methylpyrrolidinone.

25. The kit of claim 24, wherein said water-miscible organic solvent is ethanol.

26. The kit of claim 23, wherein said stannous salt is selected from the group consisting of stannous chloride, stannous iodide, stannous bromide, stannous fluoride and stannous acetate.

27. The kit of claim 26, wherein said stannous salt is stannous chloride.

28. The kit of claim 23, wherein said buffer solution is selected from the group consisting of phosphate buffer, acetate buffer, isotonic saline, citrate buffer, Tris buffer and Tris EDTA buffer.

29. The kit of claim 28, wherein said buffer solution is phosphate-buffered saline.

30. The kit of claim 23, wherein the biomolecule is selected from the group consisting of a whole molecule protein, a protein fragment and a peptide.

31. The kit of claim 30, wherein the biomolecule is a monoclonal or polyclonal antibody.

32. A method for imaging tissue of a mammal patient or subject, comprising administering to said patient or subject the product of admixing a radionuclide with a composition prepared by a method comprising the steps of:
   (a) admixing a mixture of a stannous salt and a water-miscible organic solvent with a first buffer solution to afford a tin composition;
   (b) admixing the tin composition with a sulfhydryl group-bearing biomolecule to afford a tin/biomolecule mixture; and
   (c) lyophilizing the tin/biomolecule mixture,, with the proviso that the stannous salt is not $Sn(OH)_2$.

33. The method of claim 32, wherein the radionuclide is dissolved in a second buffer solution.

34. The method of claim 33, wherein said second buffer solution is selected from the group consisting of phosphate buffer, acetate buffer, isotonic saline, citrate buffer, Tris buffer and Tris EDTA buffer.

35. The method of claim 34, wherein said second buffer solution is isotonic saline.

36. The method of claim 32, wherein said water-miscible organic solvent is selected from the group consisting of methanol, ethanol, n-propanol, iso-propanol, isobutanol, sec-butanol, dimethylsulfoxide, dimethylformamide, and N-methylpyrrolidinone.

37. The method of claim 36, wherein said water-miscible organic solvent is ethanol.

38. The method of claim 32, wherein said stannous salt is selected from the group consisting of stannous chloride, stannous iodide, stannous bromide, stannous fluoride and stannous acetate.

39. The method of claim 38, wherein said stannous salt is stannous chloride.

40. The method of claim 32, wherein said first buffer solution is selected from the group consisting of phosphate buffer, acetate buffer, isotonic saline, citrate buffer, Tris buffer and Tris EDTA buffer.

41. The method of claim 40, wherein said first buffer solution is phosphate-buffered saline.

42. The method of claim 32, wherein the radionuclide is selected from the group consisting of technetium-99m and rhenium-186m.

43. The method of claim 42, wherein the technetium-99m is in the form of a salt of pertechnetate-99m.

44. The method of claim 43, wherein the rhenium-186m is in the form of a salt of perrhenate-186m.

45. The method of claim 32, wherein said tissue selected from the group consisting of tumors, infectious lesions, microorganisms, blood clots, myocardial infarctions, atherosclerotic plaque, and normal organs and tissues.

* * * * *